United States Patent [19]

Drabek et al.

[11] Patent Number: 4,980,506
[45] Date of Patent: Dec. 25, 1990

[54] BENZOYLPHENYLUREAS

[75] Inventors: Jozef Drabek, Oberwil, Switzerland; Manfred Böger, Weil am Rhein, Fed. Rep. of Germany

[73] Assignee: Ciba-Geigy Corporation, Ardsley, N.Y.

[21] Appl. No.: 262,121

[22] Filed: Oct. 24, 1988

Related U.S. Application Data

[60] Division of Ser. No. 058,631, Jun. 4, 1987, Pat. No. 4,798,837, which is a continuation of Ser. No. 786,418, Oct. 10, 1985, abandoned.

[30] Foreign Application Priority Data

| Oct. 18, 1984 | [CH] | Switzerland | 4993/84 |
| Nov. 8, 1984 | [CH] | Switzerland | 5361/84 |
| May 14, 1985 | [CH] | Switzerland | 2048/85 |
| Aug. 14, 1985 | [CH] | Switzerland | 3502/85 |

[51] Int. Cl.$^5$ .......................................... C07C 217/84
[52] U.S. Cl. ........................................................ 564/442
[58] Field of Search .............................. 564/23, 44, 442; 514/584, 594

[56] References Cited

U.S. PATENT DOCUMENTS

| 4,013,452 | 3/1977 | Scherer et al. | 71/120 |
| 4,013,717 | 3/1977 | Wellinga et al. | 564/44 |
| 4,276,310 | 6/1981 | Sirrenberg et al. | 564/44 X |
| 4,348,412 | 9/1982 | Ehrenfreund | 564/44 X |
| 4,468,405 | 8/1984 | Rigterink et al. | 514/594 |
| 4,518,804 | 5/1985 | Rigterink et al. | 564/442 |

FOREIGN PATENT DOCUMENTS

| 71279 | 2/1983 | European Pat. Off. | 564/44 |
| 136745 | 4/1985 | European Pat. Off. | 564/44 |
| 2726684 | 1/1979 | Fed. Rep. of Germany | 564/44 |
| 2848794 | 5/1980 | Fed. Rep. of Germany | 564/44 |
| 3217619 | 11/1983 | Fed. Rep. of Germany | 564/44 |

*Primary Examiner*—Carolyn Elmore
*Attorney, Agent, or Firm*—Kevin T. Mansfield; Edward McC. Roberts

[57] ABSTRACT

The invention relates to novel substituted N-benzoyl-N'-2,5-dichloro-4-hexafluoropropyloxyphenylureas of the formula

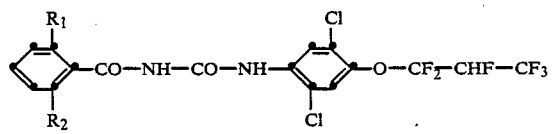

wherein $R_1$ is hydrogen, fluorine, chlorine or methoxy, and $R_2$ is fluorine, chlorine or methoxy, and to the salts thereof; to processes and intermediates for the preparation of these compounds and to compositions containing the novel compounds for controlling insects and representatives of the order Acarina, in particular plant-destructive insects.

1 Claim, No Drawings

BENZOYLPHENYLUREAS

This application is a division of Ser. No. 058,631, filed June 4, 1987, now U.S. Pat. No. 4,798,837, which is a continuation of Ser. No. 786,418, filed Oct. 10, 1985 abandoned.

The present invention relates to novel substituted N-benzoyl-N'-2,5-dichloro-4-hexafluoropropyloxy-phenylureas, to processes and to intermediates for the preparation thereof, and to the use of the novel compounds in pest control.

The invention relates to compounds of formula I

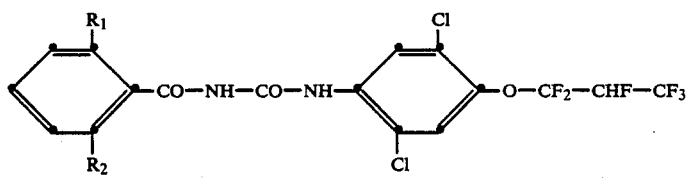

wherein $R_1$ is hydrogen, fluorine, chlorine or methoxy and $R_2$ is fluorine, chlorine or methoxy, and to salts thereof.

Compounds of formula I meriting particular interest are those wherein $R_1$ is hydrogen, fluorine or chlorine and $R_2$ is fluorine, chlorine or methoxy.

Further compounds of formula I meriting particular interest are those wherein $R_1$ and $R_2$ are simultaneously fluorine, chlorine or methoxy.

Still further preferred compounds of formula I are those wherein $R_1$ is hydrogen, fluorine or chlorine and $R_2$ is fluorine or chlorine, as well as those compounds wherein $R_1$ is hydrogen or fluorine and $R_2$ is fluorine or chlorine.

The compounds of formula I can be prepared by methods analogous to ones known per se (q.v. for example German Offenlegungsschrift specifications Nos. 2 123 236, 2 061 780 and 3 240 975).

Thus, for example, a compound of formula I can be obtained by reacting (a) the compound of formula II

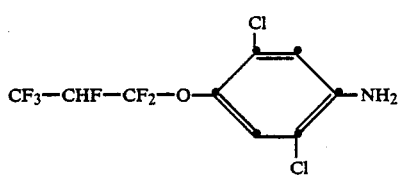

with a compound of formula III

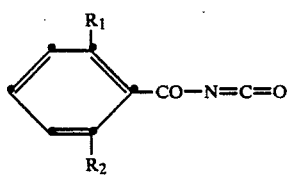

or (b) the compound of formula IV

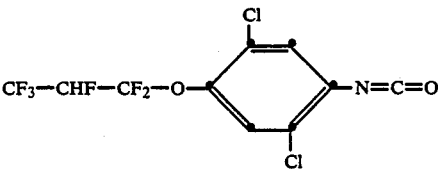

with a compound of formula V

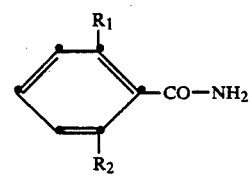

or (c) the compound of formula II with a compound of formula VI

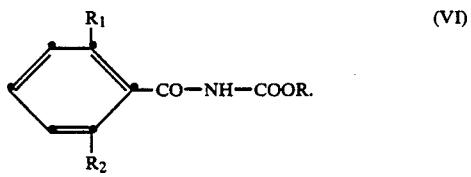

In formulae III, V and VI above, $R_1$ and $R_2$ are as defined for formula I, and R is a $C_1$–$C_8$alkyl radical which is unsubstituted or substituted by halogen, preferably chlorine.

The above processes (a), (b) and (c) can preferably be carried out under normal pressure and in the presence of an organic solvent or diluent. Examples of suitable solvents or diluents are: ethers and ethereal compounds, such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; dimethyl sulfoxide; and ketones, e.g. acetone, methyl ethyl ketone, methyl isopropyl ketone and methyl isobutyl ketone. process (a) is normally carried out in the temperature range from $-10°$ to $+200°$ C., preferably from $0°$ to $100°$ C., e.g at room temperature, and, if desired in the presence of an organic base, e.g. triethylamine. Process (b) is carried out in the temperature range from $0°$ to $150°$ C., preferably at the boiling point of the solvent employed and, if desired, in the presence of an organic base such as pyridine, and/or with the addition of an alkali metal or alkaline earth metal, preferably sodium. For process (c), i.e for the reaction of the urethane of formula VI with an aniline of formula II, a temperature range from about 60° to the boiling point of the reaction mixture is preferred, and the solvent employed is preferably an aromatic hydrocarbon such as toluene, xylene, chlorobenzene and the like.

The starting materials of formulae III and V are known and can be prepared by methods analogous to known ones. The starting aniline of formula II is a novel compound which likewise constitutes an object of the present invention. The compound of formula II can be prepared in a manner known per se by hydrogenating the suitably substituted nitrobenzene of formula VII

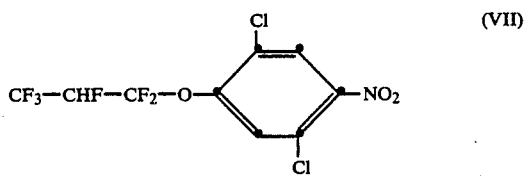

(VII)

by a process analogous to that described in J. Org. Chem. 29 (1964), 1, (q.v. also the literature cited therein). However, the aniline of formula II can also be obtained by chemical reduction (e.g. with Sn(II) chloride/HCl) of the nitro compound of formula VII (q.v. Houben-Weyl, "Methoden d. org. Chemie" 11/1, 422). The nitro compound of formula VII itself can be prepared by haloalkylating 2,5-dichloro-4-nitrophenol. A further process for the preparation of the aniline of formula II comprises haloalkylating in corresponding manner acylated 2,5-dichloro-4-hydroxyaniline and then removing the acyl group, e.g. by acid hydrolysis, or effecting the haloalkylation with a salt of 2,5-dichloro-4-hydroxyaniline, e.g. the chlorohydrate.

Benzoylisocyanates of formula III can be obtained, inter alia, as follows (q.v. J. Agr. Food Chem. 21, 348 and 993; 1973):

(III)

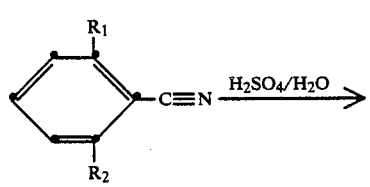

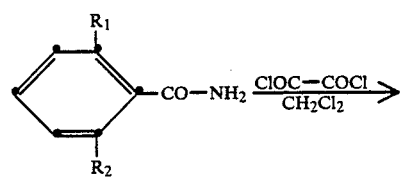

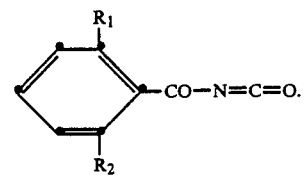

The 4-(hexafluoropropyloxy)phenylisocyanate of formula IV (b.p. 95° C./0.01 torr), which is novel per se, can be prepared e.g. by phosgenating the aniline of formula II by methods which are commonly employed in the art and also comprises an object of this invention. The benazmides of formula V which are further used as starting materials are known (q.v. for example Beilstein "Handbuch der organischen Chemie", Vol. 9, p. 336).

Urethanes of formula VI can be obtained in a manner known per se by reacting a benzoylisocyanate of formula III with a suitable alcohol or by reacting a benzamide of formula V, in the presence of a base, with a corresponding ester of chloroformic acid Cl-COOR.

In accordance with the present invention, the novel compounds of formula I also comprise the salts thereof which not only exhibit high insecticidal activity, but are also readily soluble in solvents and diluents, in particular in organic solvents, and can also be formulated more easily.

To be singled out for special mention are the metal salts of the compounds of formula I of the invention, in particular the alkali metal and alkaline earth metal salts thereof, preferably the sodium salts and potassium salts. These salts are prepared in a manner known per se, e.g. by reacting a compound of formula I with a metal alkanolate such as sodium ethylate or potassium methylate. A given salt can be converted into a desired salt of another metal by inter-reaction, e.g. with another alkanolate.

Of particular importance are the salts of compounds of formula I with organic bases, an essential feature of which is the presence of quaternary nitrogen atom. Such salts are of formula Ia

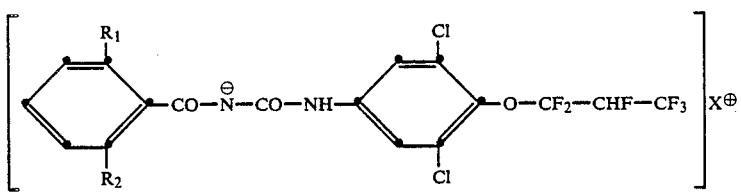

wherein $R_1$ and $R_2$ are as defined above and $X^\oplus$ is the cation of an organic base. $X^\oplus$ is preferably one of the following organic cations:

$(CH_3)_4N^\oplus$, $(C_2H_5)_4N^\oplus$, $(n-C_3H_7)_4N^\oplus$, $(i-C_3H_7)_4N^\oplus$, $(n-C_4H_9)_4N^\oplus$, (⌬—CH₂) $(CH_3)_3N^\oplus$,

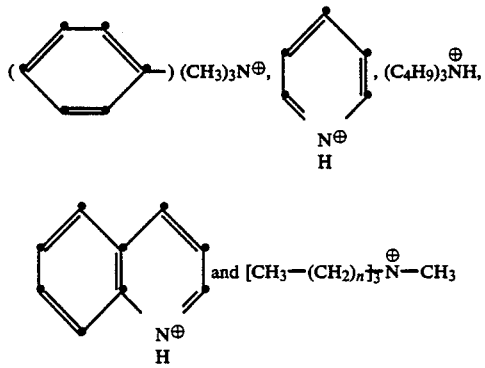

whereby n is an integer from 8 to 12. The salts of formula Ia also comprise mixtures of these salts with different cations. The salts of formula Ia can be prepared in a manner known per se by reacting a compound of formula I with corresponding ammonium hydroxides of the formula $X^{\oplus}(OH)^{\ominus}$, wherein $X^{\ominus}$ is as defined above.

Surprisingly, it has been found that the compounds of this invention and the salts thereof have excellent properties as pesticides while being well tolerated by plants and having low toxicity to warm-blooded animals. They are particularly suitable for controlling insects and representatives of the order Acarina that attack plants and animals.

In particular, the compounds of formula I are suitable for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina of the families Ixodidae, Argasidae, Tetranychidae and Dermanyssidae.

In addition to their action against flies, e.g. *Musca domestica*, and mosquito larvae, the compounds of formula I are also suitable for controlling plant-destructive feeding insects in ornamentals and crops of useful plants, especially in cotton (e.g. against *Spodoptera littoralis* and *Heliothis virescens*) and in fruit and vegetables (e.g. against *Laspeyresia pomonella, Leptinotarsa decemlineata* and *Epilachna varivestis*). The compounds of formula I have a pronounced ovicidal and, in particular, larvicidal action against insects, especially against larvae of noxious feeding insects. If compounds of formula I are ingested by adult insect stages with the feed, then a diminished oviposition and/or reduced hatching rate is observed in many insects, especially in Coleopterae, e.g. *Anthonomus grandis*.

The compounds of formula I can also be used for controlling ectoparasites such as *Lucilia sericata*, in domestic animals and productive livestock, e.g. by treating animals, cowsheds, barns, stables etc., and pastures.

The compounds of formula I are also suitable for controlling the following species of mites which attack crops of fruit and vegetables: *Tetranychus urticae, Tetranychus cinnabarinus, Panonychus ulmi, Broybia rubrioculus, Panonychus citri, Eriophyes piri, Eriophyes ribis, Eriophyes vitis, Tarsonemus pallidus, Phyllocoptes vitis* and *Phyllocoptruta oleivora*.

The good pesticidal activity of the compounds of formula I of the invention corresponds to a mortality of at least 50–60 % of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives nd the prevailing circumstances The formulations, i.e. the compositions, preparations or mixtures containing the compound (active ingredient) of the formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkalins earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, New Jersey, 1979; Dr. Helmut Stache, "Tensid Taschenbuch" (Handbook of Surfactants), Carl Hanser Verlag, Munich/Vienna.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1:

(a) Preparation of 2,5-dichloro-4-(1,1,2,3,3,3-hexafluoropropyloxy)aniline 47 g of 4-acetylamino-2,5-dichlorophenol together with 154 g of 90% potassium hydroxide solution and 130 ml of dimethylformamide are stirred in an autoclave. 75.8 g of hexafluoropropylene are then pressed into the closed autoclave. The mixture is stirred for 20 hours at 70° C. under the pressure existing in the autoclave. After cooling, the mixture is concentrated by rotary evaporation and the residue is dissolved in methylene chloride. The resultant solution is washed with water, dried over $Na_2SO_4$ and concentrated. The crude product obtained as residue is chromatographed through a column of silica gel (length: 1 m; diameter: 10 cm) eluted with an 11:1 mixture of toluene and acetone, affording 4-acetylamino-2,5-dichloro-1-(1,1,2,3,3,3-hexafluoropropyloxy)benzene in the form of pale yellow crystals (m.p.: 93°–95° C.), 26 g of which are kept for 10 hours under reflux with 110 ml of ethanol and 35.6 ml of 37% hydrochloric acid. The reaction mixture is then concentrated, diluted with ice/water and made weakly alkaline. The product is extracted from the mixture with methylene chloride. The organic extract phase is washed with water, dried over $Na_2SO_4$ and concentrated. The residue is purified by distillation, thus affording the title compound of the formula

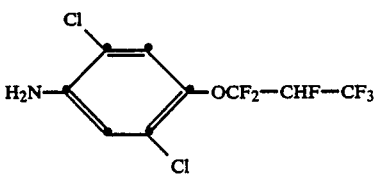

as a colourless liquid with a boiling point of 81°–83° C./0.05 torr.

(b) Preparation of N-(2,6-trifluorobenzoyl)-N'-[2,5-dichloro-4(1,1,2,3,3,3-hexafluoropropyloxy)phenyl]urea 4.7 g of 2,5-dichloro-4-(1,1,2,3,3,3-hexafluoropropyloxy)aniline are dissolved with stirring in 50 ml of dry toluene and, with exclusion of moisture, a solution of 2.62 g of 2,6-difluorobenzoylisocyanate in 10 ml of dry toluene is added at room temperature. The batch is stirred for a further 10 hours at room temperature. About 75% of the solvent is then removed by rotary evaporation, the precipitated residue is filtered with suction, washed with a small amount of cold toluene and hexane and then dried in vacuo, affording the title compound of the formula

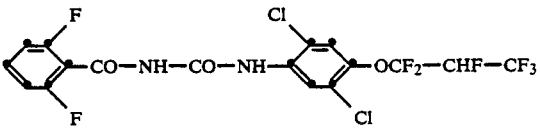

in the form of a crystalline white powder with a melting point of 174°–175° C. (compound 1).

The following compounds of formula I have been prepared in a manner corresponding to that described above:

| Compound | | m.p. |
|---|---|---|
| 2 | 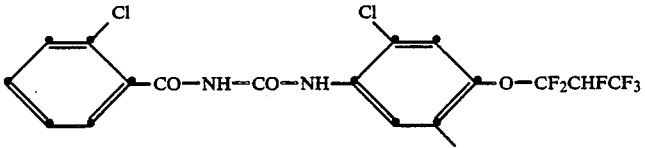 | 165–166° C. |
| 3 | 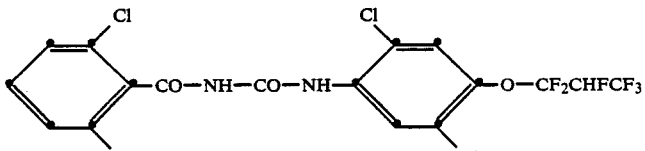 | 188–190° C. |
| 4 | 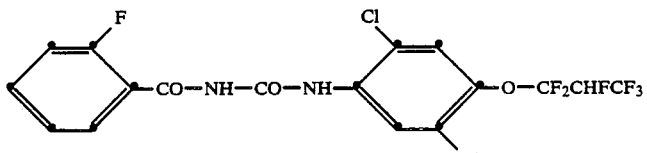 | 143–145° C. |
| 5 | 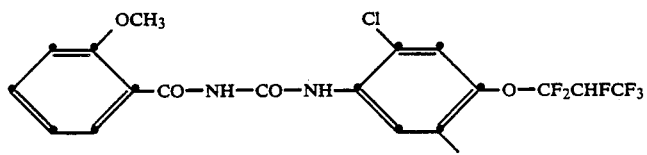 | 135–137° C. |
| 6 | 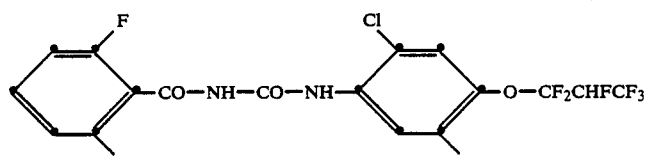 | 176–177° C. |
| 7 | 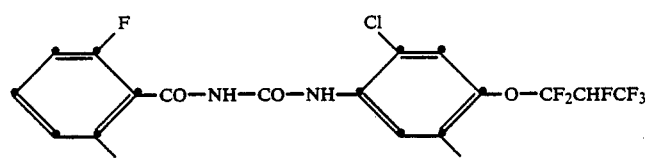 | 177–178° C. |

| Compound | m.p. |
|---|---|
| 8 ![structure] | 162–163° C. |
| 9 ![structure] | 190–191° C. |

(c) Preparation of the sodium salt of compound 1

9.58 g of N-(2,6-difluorobenzoyl)-N'-[2,5-dichloro-4-(1,1,2,3,3,3-hexafluoropropyloxy)phenyl]urea are suspended in 20 ml of absolute methanol. A solution of 0.43 g of sodium in 30 ml of absolute methanol is added dropwise with stirring to this suspension. A clear solution forms which is then concentrated. The residual product is dried in vacuo at room temperature, affording the title compound in the form of colourless crystals of the formula

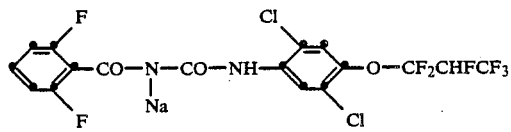

with a melting point of 169°–171° C. under decomposition (compound 10).

The following salt of compound 2 of the formula below can also be prepared by proceeding as described above:

| Compound | m.p. |
|---|---|
| 11 ![structure] | from 140° C./ decomposition |

(d) Preparation of the tetrabutylammonium salt of compound 1

2.56 g of N-(2,6-difluorobenzoyl)-N'-[2,5-dichloro-4-(1,1,2,3,3,3-hexafluoropropyloxy)phenyl]urea are suspended in 30 ml of methanol. With stirring, 5.2 g of methanolic solution containing 1.3 g of tetra-n-butylammonium hydroxide are added to this suspension, whereupon a clear solution forms. This solution is concentrated and the residual crude product is suspended in hexane. The suspension is filtered with suction and the filter residue is washed with hexane and then dried, affording the title compound of the formula

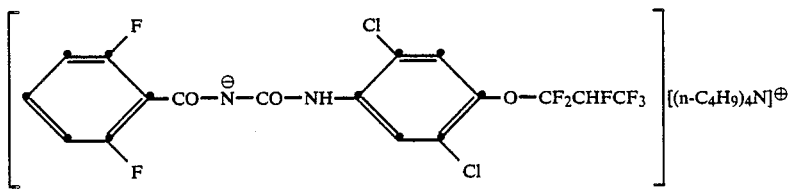

in the form of colourless crystals with a melting point of 110° C. (compound 12).

The following salts of formula Ia can also be prepared in accordance with this procedure:

Compound

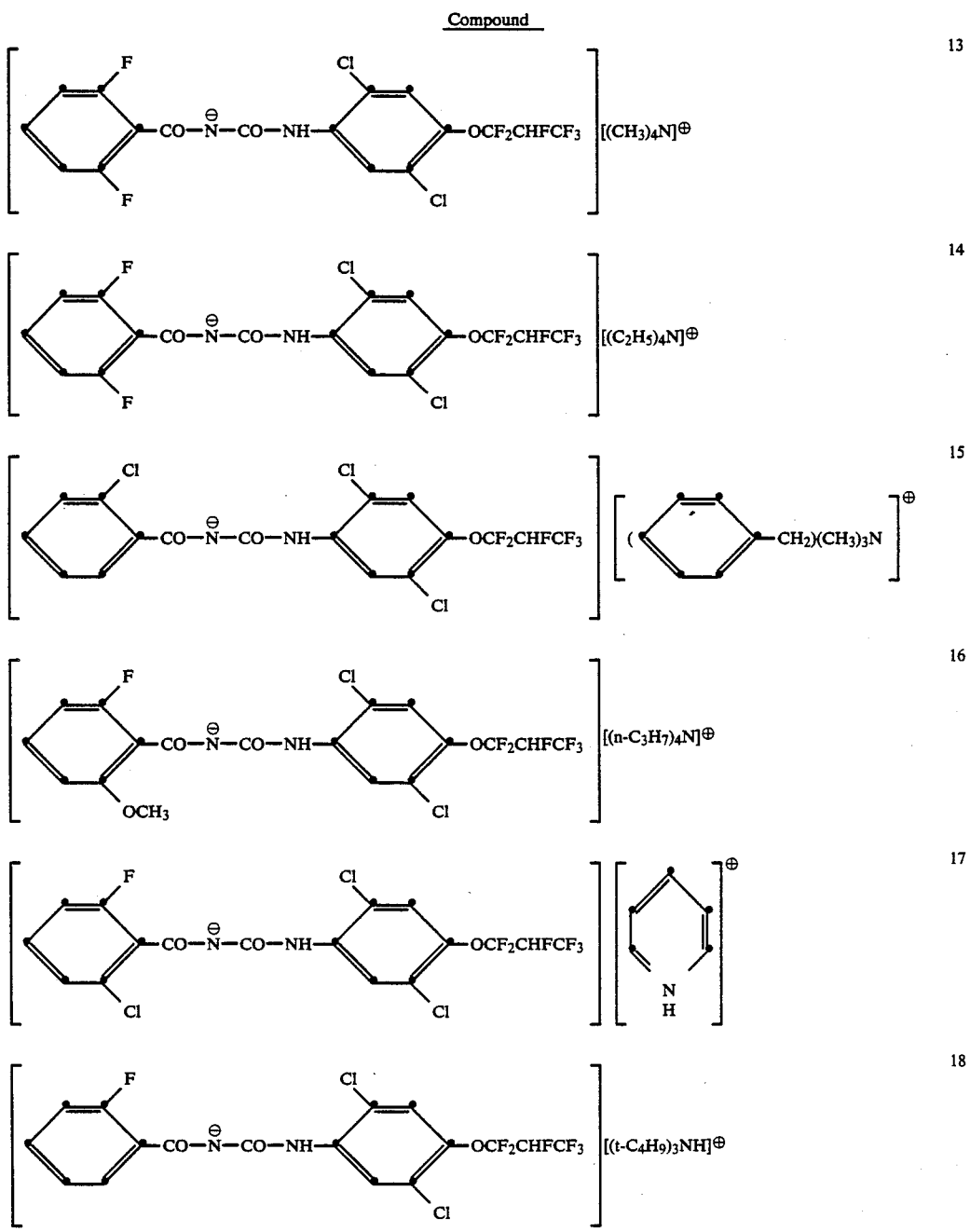

EXAMPLE 2:

Formulations for active ingredients of formula I according to Example 1 or combinations thereof with other insecticides or acaricides (throughout, percentages are by weight)

| 1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |

| -continued | | | |
|---|---|---|---|
| 1. Wettable powders | (a) | (b) | (c) |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether | 3% |

-continued

| 2. Emulsifiable concentrate | |
|---|---|
| (4–5 moles of ethylene oxide) calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentrations can be obtained from this concentrate by dilution with water.

| 3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carrier, and grinding the mixture in a suitable mill.

| 4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 5. Coated granulate | |
|---|---|
| compound of formula I or combination | 3% |
| polyethylene glycol 200 | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 3:

Action against *Musca domestica*

50 g of freshly prepared nutrient substrate for maggots are charged into each of a number of beakers. A specific amount of a 1% acetonic solution of the respective test compound is pipetted onto the nutrient substrate present in the beakers to give an active ingredient concentration of 800 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I according to Example 1 have good activity in this test.

EXAMPLE 4:

Action against *Lucilia sericata*

1 ml of an aqueous solution containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of formula I according to Example 1 exhibit good activity against *Lucilia sericata*.

EXAMPLE 5:

Action against *Aedes aegypti*

A concentration of 800 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 1, 2 and 5 days.

In this test, compounds of formula I according to Example 1 exhibit good activity against *Aedes aegypti*.

EXAMPLE 6:

Insecticidal action against feeding insects

Cotton plants about 25 cm high, in pots, are sprayed with aqueous emulsions which contain the respective test compound in concentrations of 0.75, 12,5 and 100 ppm. After the spray coating has dried, the cotton plants are populated with *Spodoptera littoralis* and *Heliothis virescens* larvae in the L$_3$-stage. The test is carried out at 24° C. and 60% relative humidity. The percentage mortality of the test insects is determined after 120 hours.

Compound 1 according to Example 1 effects 80 to 100% mortality against Spodoptera larvae and Heliothis larvae at 0.75 ppm. Compound 3 effects 80 to 100% mortality against Spodoptera larvae at 12.5 ppm and against Heliothis larvae at 100 ppm.

EXAMPLE 7:

Action against *Epilachna varivestis*

*Phaseolus vulgaris* plants (dwarf beans) about 15-20 cm in height are sprayed with aqueous emulsion formulations of the test compound in a concentration of 800 ppm. After the spray coating has dried, each plant is populated with 5 larvae of *Epilachna varivestis* (Mexican bean beetle) in the $L_4$-stage. A plastic cylinder is slipped over the treated plants and covered with a copper gauze top. The test is carried out at 28° C. and 60% relative humidity. The percentage mortality is determined after 2 and 3 days. Evaluation of feeding damage (anti-feeding effect), and of inhibition of development and shedding, is made by observing the test insects for a further 3 days.

The compounds of formula I according to Example 1 exhibit good activity in this test.

EXAMPLE 8:

Ovicidal action against *Heliothis virescens*

Corresponding amounts of a wettable powder formulation containing 25% by weight of the test compound are mixed with sufficient water to produce an aqueous emulsion with an active ingredient concentration of 800 ppm. One-day-old egg deposits of Heliothis on cellophane are immersed in these emulsions for 3 minutes and then collected by suction on round filters. The treated deposits are placed in petri dishes and kept in the dark. The hatching rate in comparison with untreated controls is determined after 6 to 8 days.

The compounds of formula I according to Example 1 exhibit good activity in this test.

EXAMPLE 9

Action against *Laspeyresia pomonella* (eggs):

Egg deposits of *Laspeyresia pomonella* not more than 24 hours old are immersed on filter paper for 1 minute in an aqueous acetonic solution containing 800 ppm of the test compound.

After the solution has dried, the eggs are placed in petri dishes and kept at a temperature of 28° C. The percentage of larvae hatched from the treated eggs and the percentage mortality is evaluated after 6 days.

The compounds of formula I according to Example 1 exhibit good activity in this test.

EXAMPLE 10:

Influence on the reproduction of *Anthonomous grandis*

*Anthonomous grandis* adults which are not more than 24 hours old after hatching are transferred in groups of 25 to barred cages. The cages are then immersed for 5 to 10 seconds in an acetonic solution containing 400 pm of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine the percentage mortality of the eggs, i.e. the number of larvae which have developed from the eggs.

The duration of the reproduction inhibiting effect of the test compounds is determined by monitoring the egg deposits further, i.e. over a period of about 4 weeks. Evaluation is made by assessing the reduction in the number of deposited eggs and hatched larvae in comparison with untreated controls.

Compounds 1 and 3 according to Example 1 exhibit an 80 to 100% ovicidal activity in this test.

EXAMPLE 11:

Action against *Anthonomus grandis* (adults)

Two cotton plants in the 6-leaf stage, in pots, are each sprayed with a wettable aqueous emulsion formulation containing 400 ppm of the test compound. After the spray coating has dried (about 1½ hours), each plant is populated with 10 adult beetles (*Anthonomus grandis*).

Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds of formula I according to Example 1 exhibit good activity in this test.

What is claimed is:

1. The compound of formula II

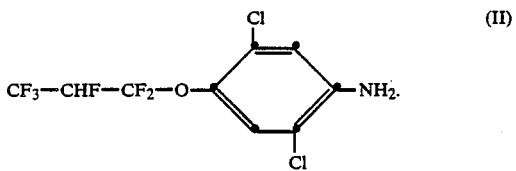

(II)

* * * * *